United States Patent [19]

Jokinen

[11] Patent Number: 5,706,090

[45] Date of Patent: Jan. 6, 1998

[54] METHOD FOR POSITIONING A CONTAINER FOR MEASUREMENT OF WEAR IN THE CONTAINER LINING

[75] Inventor: Hannu Jokinen, Oulunsalo, Finland

[73] Assignee: Spectra-Physics Visiontech Oy, Oulu, Finland

[21] Appl. No.: 629,145

[22] Filed: Apr. 8, 1996

[30] Foreign Application Priority Data

Apr. 13, 1995 [FI] Finland .................................. 951810

[51] Int. Cl.⁶ ........................... G01B 11/24; G01B 11/00
[52] U.S. Cl. ............................................. 356/376; 356/394
[58] Field of Search .................................. 356/394, 376, 356/375, 3.1, 141.2, 139.03

[56] References Cited

U.S. PATENT DOCUMENTS 5,125,745   6/1992   Neiheisel et al. .................... 356/376

FOREIGN PATENT DOCUMENTS

WO/9218829   10/1992   European Pat. Off. .

*Primary Examiner*—Frank G. Font
*Assistant Examiner*—Amanda Merlino
*Attorney, Agent, or Firm*—Sughrue, Mion, Zinn, Macpeak & Seas, PLLC

[57] ABSTRACT

The invention relates to a method for positioning a container for measurement of wear in the container lining. The method comprises taking a reference picture by a camera means of a set of at least three reference marks mounted on the container, and performing reference measurement of the container lining with a measuring device emitting and receiving optical radiation. Later, in the actual measurement situation, a measurement picture is taken of the set of reference marks with the camera means, and the actual measurement of the wear in the container lining is performed with the measurement device emitting and receiving optical radiation. By comparing the measurement situation picture with the reference picture, correction factors are calculated, on the basis of which the actual measurement of the wear in the container lining and the previously made reference measurement of the container lining are combined so as to be represented in the same coordinate system.

17 Claims, 5 Drawing Sheets

METHOD FOR POSITIONING A CONTAINER FOR MEASUREMENT OF WEAR IN THE CONTAINER LINING

BACKGROUND OF THE INVENTION

This invention relates to a method for positioning a container for measurement of wear in the container lining.

The present invention can be applied to measurements of wear in the linings of containers, particularly ladles, used in the metallurgic industry.

The wear in a lining is generally measured by a method based on measuring the propagation time or phase difference of a laser beam: the laser beam is directed to the lining on the inner surface of a converter, from which it is reflected back to the measuring device. In the method based on measuring the propagation time, the distance between the measuring device and each measured point on the lining to be measured in the coordinate system of the measuring device can be calculated on the basis of the time difference between the emitting time and the return time of the laser beam. The measured points define the wear profile of the lining, which may be output for instance to a display terminal, by which the wear profile measured from a container in use can be compared graphically and numerically with the profile that was measured of the inner surface of the same container during the modelling step before the container was actually brought into use, i.e. before the first melting.

To measure wear in the lining of three-dimensional objects, such as ladles and other containers used in the steel industry, by non-contacting methods, such as laser measurement, requires that the measuring device and the container be represented in the same coordinate system. Combining the coordinate systems of the measuring device and the container is called fixing. In other words, the measuring device is positioned in relation to the object. For the fixing, it is necessary to use at least three fixing points, or reference marks.

In the known methods, fixing is performed by using fixing points mounted in the vicinity of the container opening. The laser beam emitted by the measuring device is directed to these fixing points in turn, and the coordinates of the fixing points in the coordinate system of the measuring device are measured on the basis of them. In the known methods, the container to be measured and the measuring device can be represented in the same coordinate system by measuring at a time the fixing points and the actual points in the lining which are to be measured. In the known methods, the laser beam emitted by the measuring device is directed to the fixing points manually, for instance by means of binoculars or some other instrument. In these known methods, the aim is to direct the laser beam manually to the centre of the fixing point; in order that the fixing could succeed, the operators of the measuring device are thus required to perform several operations before all fixing points have been measured. The drawback of these known methods is that it is difficult to automate the fixing operation; in addition, when the fixing is performed by a human being, there is a risk of errors in both the estimation of the centre of the fixing point and the actual directing step. The Applicant's own previous application FI 932339 discloses a method of the type described above, where the fixing points, or reference marks, are mounted on the bottom of the container, not in the vicinity of the container opening, where they have been positioned before.

Particularly when the container is a ladle, a further problem is caused by the fact that a ladle brought to the measuring site is always in a slightly different location and position than the previous time on account of impurities and stresses to which the structures supporting the container or the container parts bearing against them are subjected.

SUMMARY OF THE INVENTION

The object of the present invention is to provide a new type of method which obviates the problems associated with the known solutions.

This is achieved with a method of the invention, which is characterized in that it comprises taking a reference picture with a camera means of a set of at least three reference marks mounted on the container and performing reference measurement of the container lining with a measuring device emitting and receiving optical radiation, and later in the actual measurement situation, taking a measurement picture of the set of reference marks with the camera means, and performing the actual measurement of the wear in the container lining with the measurement device emitting and receiving optical radiation, and by comparing the measurement picture with the reference picture, calculating correction factors, on the basis of which the actual measurement of the wear in the container lining and the previously made reference measurement of the container lining are combined so as to be represented in the same coordinate system.

The method of the invention has several advantages. By means of the method, it is easy to obviate the problems caused by the fact that the location of the container is always slightly different from the previous measurement. The location of the container is determined on the basis of calculations done by an apparatus, not on the basis of ocular directing operations performed by a human being. The method is reliable and can always be repeated in the same way. The method of the invention eliminates sources of error caused by a human being, and thus improves the chances of success of the measurement. The reliability of the actual lining measurement is therefore improved, which also results in financial savings, as the service life of container linings can be more efficiently optimized. In addition, the method can be automated to a greater extent and more easily than the known methods. By applying the method, it is also possible to perform calibration in a simple and reliable manner.

BRIEF DESCRIPTION OF THE DRAWINGS

In the following, the invention will be described more closely with reference to the accompanying drawings, in which.

DETAILED DESCRIPTION OF THE PREFERRED EMBODIMENTS

With reference to the figures, the main components of the measuring arrangement are a camera means 1, a measuring device 2 emitting and receiving optical radiation, a container 3, and a set P of reference marks, or reference points, mounted on the container. The container 3 is a ladle. The container 3 is thus provided with a set P of reference marks P1, P2, P3 and P4, which are preferably attached to the side of the container 3. In the figure, the reference marks P1–P4 are mounted on a reference mark element P, or reference mark plate P. The main parts of the camera means are optics 1a, an image plane 1b and a stand 2c.

The container 3, or ladle 3, comprises a bottom 3f, a wall 3b, an opening 3c and a lining 3d, 3e. Lining 3d represents new, unworn lining, whereas lining 3e represents worn lining, on the basis of which the actual measurement of wear is made. The container also comprises a bottom hatch 3f, through which the container 3 can be emptied.

The measuring arrangement is preferably provided in connection with a sanding station A. The measuring site A, i.e. the sanding station A, comprises a construction 4, such as a tower 4, in which the measuring device 2 is positioned, and support means 5, on which the container 3 can be supported by means of its support elements 6. The container 3, particularly a ladle 3, is brought to the measuring site A by a transfer device, such as an overhead cable holster.

Figure 4:
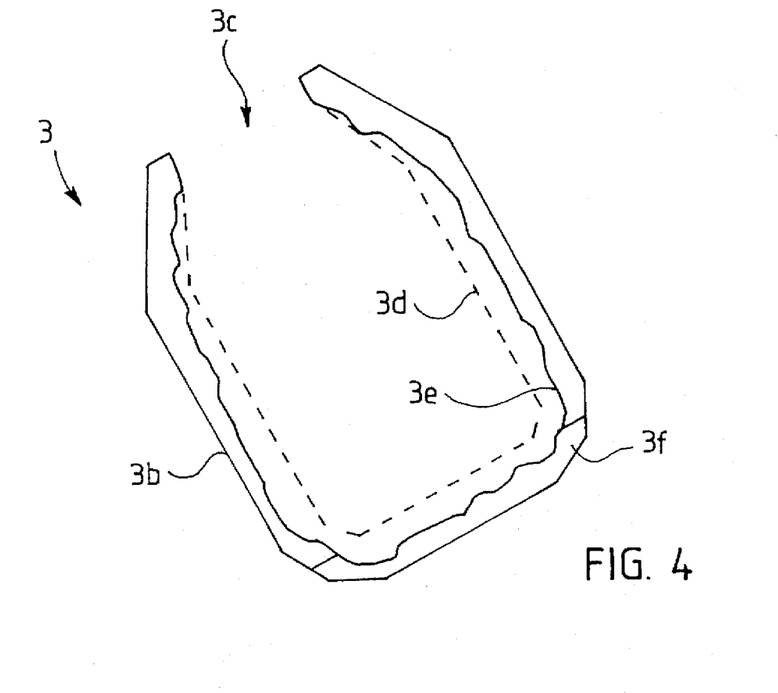
FIG. 4 is a reference diagram of a worn container as compared with an unworn one.
Figure 5:
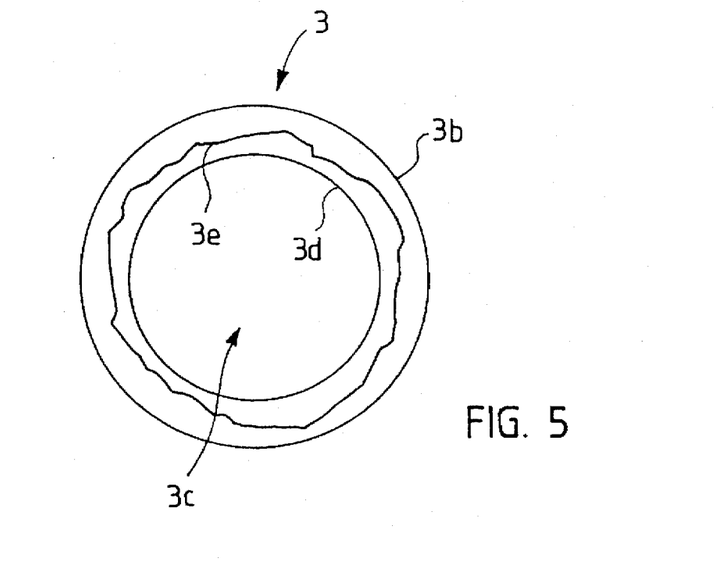
FIG. 5 is a reference diagram in accordance with FIG. 4, seen in the longitudinal direction of the container.

The camera means 1 is preferably a CCD camera, and the measuring device 2 is a device emitting and receiving optical radiation, such as laser radiation, the main component of the device being a transceiver 2a. The measuring arrangement further comprises an optical cable 2b, a calculation unit 2c, and a display device 2d. In addition, the measuring arrangement comprises a cable 2e for connecting the camera means 1 to the calculation unit 2c. The calculation unit 2c thus processes data received both from the laser measuring device 2 and from the camera 1. The display device 2d is a monitor, and the lining profiles of the container 3 shown in FIGS. 4 and 5 are displayed on its screen.

Figure 1:
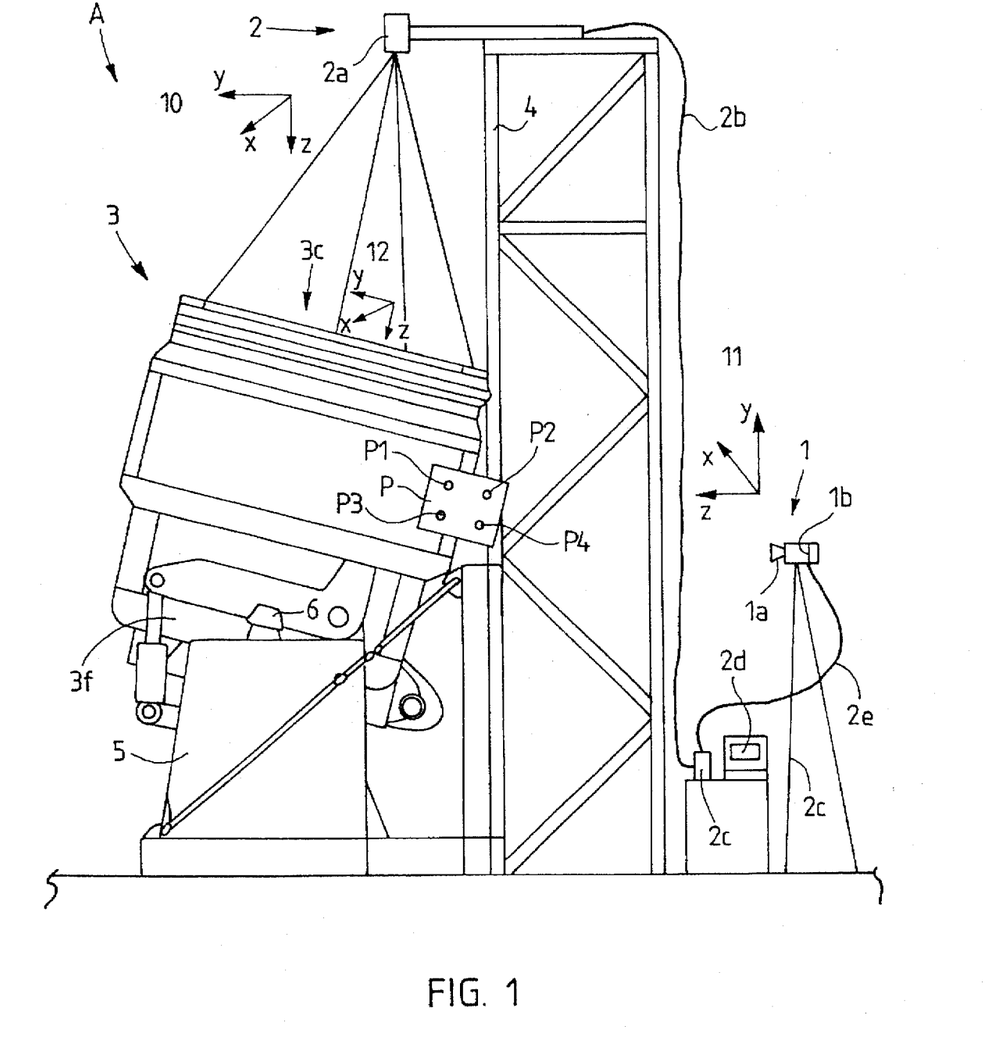
FIG. 1 shows a measuring arrangement.
Figure 6:
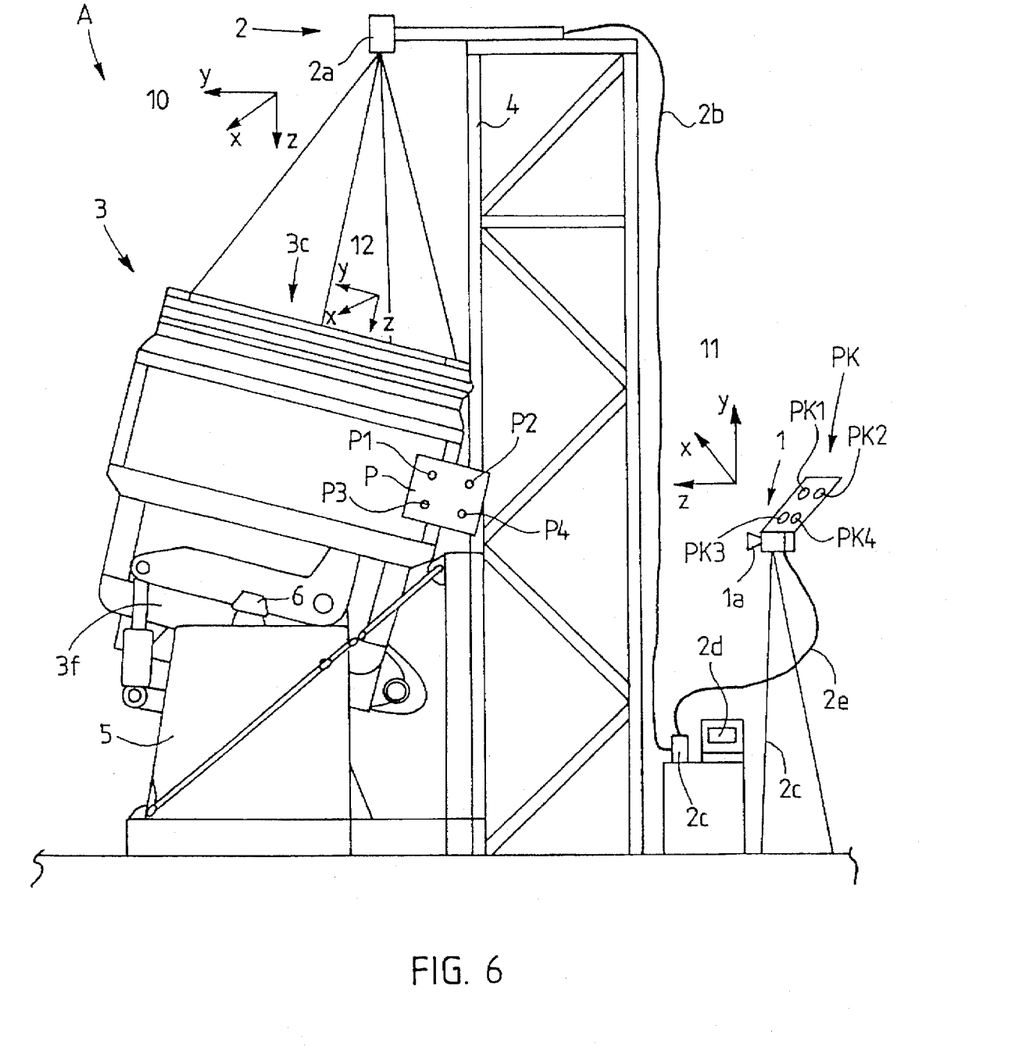
FIG. 6 shows a measuring arrangement in a first embodiment of calibration.
Figure 7:
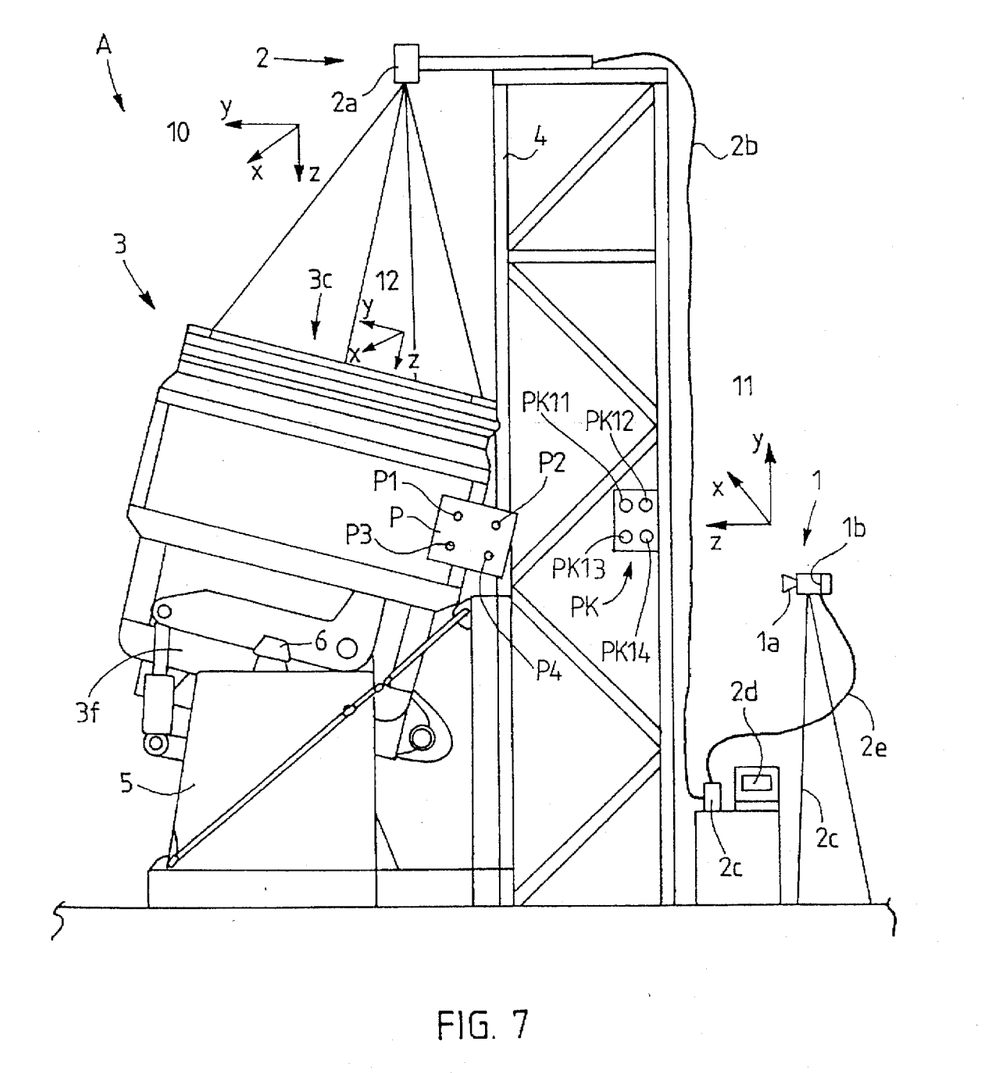
FIG. 7 shows a measuring arrangement in a second embodiment of calibration.

FIGS. 1, 6 and 7 also show the coordinate systems 10–12. Coordinate system 10 is the coordinate system of the measuring device 2 and comprises x-, y- and z-axes. Coordinate system 11 is the coordinate system of the camera 2 and comprises x-, y- and z-axes. Coordinate system 12 is the coordinate system of the object to be measured, i.e. the container 3, and comprises x-, y- and z-axes.

Figure 2:
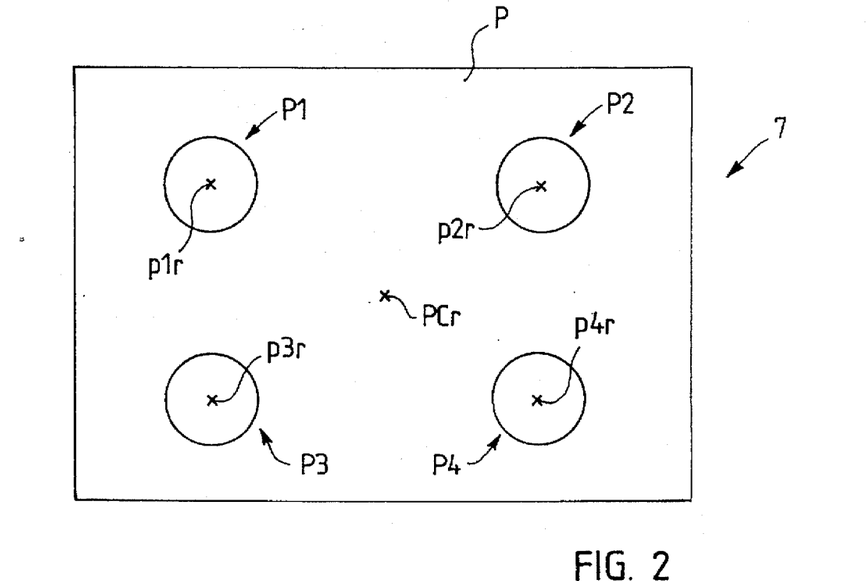
FIG. 2 shows a reference picture taken by a camera means of a set of reference marks.

The invention relates to a method for positioning a container 3 and for utilizing the positioning information in the measurement of wear in a container lining. According to the method, a reference picture 7 according to FIG. 2 is taken with the camera means 1 of a set P of at least three reference marks P1–P4 mounted on the container 3, and a reference measurement 3d of the lining of the container 3 is made with the measuring device 2 emitting and receiving optical radiation. FIG. 2 shows the reference picture 7 of the set P of reference marks, or reference points P1–P4; FIGS. 4 and 5 illustrate reference measurement 3d of the lining.

The location of the container is the same when a reference picture 7 of the set P of reference marks P1–P4 is taken with the camera means 1 and when the reference measurement 3d of the lining is made with the measuring device 2. Preferably, the taking of the reference picture 7 of the set P of reference marks P1–P4 with the camera 1 and the reference measurement 3d of the lining made with the measuring device 2 take place at least approximately simultaneously or successively within a relatively short time; this ensures that taking a reference picture 7 of the set of reference marks P1–P4 and the reference measurement 3d of the lining are measurements comparable, or bound, to each other.

Figure 3:
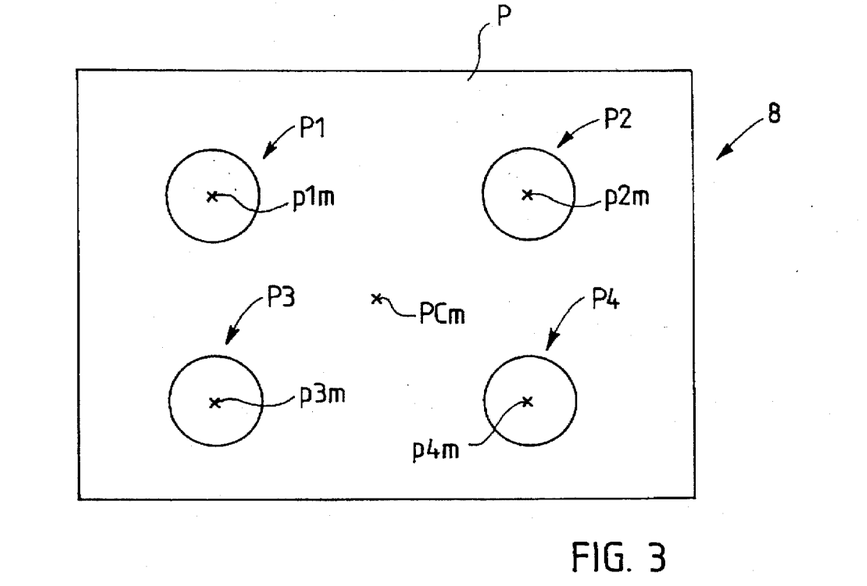
FIG. 3 shows a measurement picture taken by a camera means of the set of reference marks.

Once the reference picture 7 of the set of reference marks P1–P4 has been taken and the reference measurement 3d of the lining has been made, the container can be transferred from the measuring site A to the following process step. The container 3, or ladle 3, can be charged with material to be melted, and after various steps the molten metal can be discharged from the ladle 3 through the bottom hatch 3f; after this, the ladle, whose lining is now slightly worn, is brought again to the measuring site A. According to the method of the invention, a measurement picture 8 according to FIG. 3 is taken of the set P of reference marks P1–P4 with a camera means 1 in the actual measuring situation, and the actual measurement 3e of the wear in the container lining is made with the measuring device 2. The method of the invention further comprises calculating correction factors by comparing the measurement picture 8 of the set of reference marks P1–P4 with the reference picture 7 of the set of reference marks P1–P4. On the basis of these correction factors, the actual measurement 3e of the wear in the worn container lining and the previously made reference measurement 3d of the unworn lining are combined so as to be represented in the same coordinate system. Furthermore, the location of the container is the same when the measurement picture 8 is taken of the set P of reference marks P1–P4 and when the actual measurement 3e of the wear in the container lining is made. Preferably, the taking of the measurement picture 8 of the set P of reference marks P1–P4 and the actual measurement 3e of the wear take place at least approximately simultaneously or successively within a relatively short time; this ensures that the taking of a measurement picture 8 of the set of reference marks P1–P4 and the actual measurement 3e of the wear in the container lining are measurements bound to each other.

The reference picture 7 of FIG. 2 shows the centres p1r, p2r, p3r and p4r of each reference mark P1–P4. Correspondingly, the measurement picture 8 of FIG. 3 shows the centres p1m, p2m, p3m and p4m of each reference mark P1–P4.

The relative location and position of the set P of reference marks P1–P4 in the coordinate system 11 of the camera means 1 are determined on the basis of both the reference picture 7 and the measurement picture 8 by image processing operations, e.g. by matrix algebra. In the reference picture 7, the coordinates of the centres of the reference marks P1–P4 in the coordinate system 11 of the camera are as follows: P1(x,y,z)r, P2(x,y,z)r, P3(x,y,z)r and P4(x,y,z)r. Correspondingly, in the measurement picture 8, the coordinates of the centres of the reference marks P1–P4 in the coordinate system 11 of the camera are as follows: P1(x,y,z)m, P2(x,y,z)m, P3(x,y,z)m and P4(x,y,z)m. These coordinates have been calculated by the calculation unit 2c. In order to find out how the location of the container in the measurement situation differs from its location in the reference situation, the method comprises determining the change in the location and position of the set of reference marks, dP1(x,y,z), dP2(x,y,z), dP3(x,y,z) and dp4(x,y,z), the correction factors D being calculated on the basis of this change. According to a preferred embodiment of the method of the invention, the location of a reference point, e.g. the centre of the set P of reference marks, in the reference picture 7 (centre PCr) and in the measurement picture 8 (centre PCm) is determined in order to determine the change in the location and position of the set P of focusing marks P1–P4. This preferred embodiment expedites the method.

In a preferred embodiment, the location of the centre of each reference mark P1–P4 is determined for determining the change in the location and position of the set P of reference marks P1–P4. Thus, P1 (x, y, z) r, P2 (x, y, z) r, P3(x,y,z)r and P4 (x, y, z) r, and P1(x,y,z)m, P2(x,y,z)m, P3(x,y,z)m and P4(x,y,z)m are the coordinates of the centres of the reference marks P1–P4. This embodiment expedites the methods, since the centres can be determined by means of simple calculations.

In a preferred embodiment of the method of the invention, the reference marks P1–P4 of which a picture is to be taken with the camera 1 are of a regular shape, preferably substantially circular, which allows them to be computationally processed in a simple manner.

The calculation unit 2c compares the reference picture 7 and the measurement picture 8, and calculates the correction factors. The calculation unit 2c calculates at first the difference between the location and position of the set of reference marks P1–P4 in the reference situation and their location and position in the current measurement situation. On the basis of these data and the known geometry of the container 3, the calculation unit 2c calculates the computational correction on the surface of the lining inside the container 3 which corresponds to the change in the location and position of the set of reference marks P1–P4. On the basis of this data, it is possible to calculate the final correction factors, which allow the measurement 3e of the wear in the lining and the previous reference measurement 3d of the lining to be represented in the same coordinate system, i.e. they make these measurements comparable to each other.

A camera means 1 is thus used in the positioning of the container 3 to measure the difference between the reference situation and the actual measurement situation. The data obtained from the camera means 1 is utilized as computational correction data in measuring the wear.

The reference measurement and the actual measurement of the wear are carried out using a method known per se and a measuring device 2. The Applicant's previous application FI 932339, which is referred to herein, discloses the use of a similar device. The solution of the present invention is, however, particularly concerned with taking pictures of the set P of reference marks P1–P4 with the camera means 1 in a reference situation and in an actual measurement situation, and with utilizing the correction data determined on the basis of the reference picture 7 and the measurement picture 8 of the set of reference marks P1–P4 for correcting the reference measurement 3d and the actual measurement 3e of the wear of the lining to make them comparable to each other, i.e. to allow them to be represented in the same coordinate system.

The calculation unit 2c is used in a manner known per se for measuring the propagation time of the laser pulse from the transmitter of the transceiver 2a of the measuring device 2 through the lining of the container 3 to the receiver of the transceiver 2a. The measurement of the propagation time allows the distance between the measuring device 2 and the hitting point on the container lining 3e of the laser beam emitted by the measuring device to be determined in the measurement of the lining. The use of several marks gives the entire profile as shown in FIGS. 4 and 5, where 3d represents the reference measurement of an unworn new lining, and 3e represents the actual measurement of the wear in a worn lining. The measurement of the lining is carried out in a manner known per se by directing the optical beam emitted by the measuring device 2 through the container opening 3c to the lining and by measuring the optical radiation reflected back. The measured worn lining 3e is compared with the lining 3d measured in the modelling step, or reference situation, as shown in FIGS. 4 and 5, for instance on the screen 4a of the display terminal shown in FIG. 1. The method of the invention allows the unworn lining 3d and the worn lining 3e to be represented in the same coordinate system using the camera means 1 and the difference calculated on the basis of the reference picture 7 and the measurement picture 8 taken by it. This difference is represented by correction factors D: dP1(x,y,z), dP2(x,y,z), dP3(x,y,z) and dP4(x,y,z).

A reference picture 7 of the set of reference marks P1–P4 is taken and reference measurement 3d of the lining is made when a container 3 with a new or renewed lining is brought to the measuring site. A measurement picture of the set of reference marks P1–P4 is taken and the actual measurement of the lining is made when a container 3 with a worn lining is brought to the measuring site A. Thus, according to the method, a reference picture 7 is taken once of the set P of reference marks P1–P4 on a new or renewed ladle 3, and reference measurement 3d, or the so-called modelling measurement, is made once of the container lining. A measurement picture 8 of the set P of reference marks P1–P4 is taken and the actual measurement 3e of the wear in the lining is made when the container is brought again to the measuring site A when its lining is worn. As regards the word "once" used above, it should be noted that it does not exclude the possibility that several reference pictures are taken in the same situation or that several reference measurements of the container lining are made in the same situation, since the use of averages makes the method more reliable.

According to a preferred embodiment of the invention, the pictures are taken of the set P of reference marks P1–P4 with the camera means 1 in such a way that the image plane 1b of the camera means 1 and the plane formed by the set P of reference marks P1–P4 are inclined in relation to each other. The inclination is effected with respect to all the three coordinate axes x, y and z. In FIGS. 1, 6 and 7, the set P of reference marks is inclined in such a way that its upper edge is closer to the image plane 1b of the camera means 1 than the lower edge of the set P of reference marks, and that for instance the right edge of the set P of reference marks is closer to the image plane 1b of the camera means 1 than the left edge. The inclination of the set P of reference marks P1–P4 with respect to the image plane 1b of the camera 1 has the advantage that the changes in the location and position of the set P of reference marks and thus also of the container can be more easily detected by the camera 1, which improves the accuracy of the method. The changes in the location and position of the set P of reference marks P1–P4 are thus projected to the image plane 1b of the camera 1 more clearly in this preferred embodiment. According to a preferred embodiment, the inclination is 20 to 45 degrees, most preferably at least approximately 40 degrees, whereby the changes are sufficiently great and the reference marks P1–P4 are still sufficiently detectable by the camera 1. The set P of reference marks P1–P4 is better protected against any splashes of slag and impacts when it is inclined as described above so that its upper edge is closer to the image plane 1b of the camera 1 than its lower edge.

According to a preferred embodiment of the method of the invention, the picture of the set P of reference marks P1–P4 is taken with the camera means 1 from a quite different direction from the measurement of the lining, made with the measuring device 2. Most preferably, the picture of the set P of reference marks P1–P4 is taken with the camera means 1 from the side, as in FIG. 1, or from below, and the lining is measured with the measuring device 2 from above. This technique is particularly suitable for measuring a ladle 3. An advantage achieved with this embodiment is that the camera 1 has a clear view of the set of reference marks P1–P4, and the laser measuring device 2 has a clear view of the lining on the inner surface of the container. Another advantage of this embodiment is that the camera 1 and the measuring device 2 are protected against any splashes of slag and excessive heat. If a picture of the set P of reference marks is taken from below, the set P of reference marks should naturally be located on the bottom of the container 3 or mounted in some other downward position.

A preferred embodiment of the method employs a camera means 1 that is stationary and has a fixed focal distance. This embodiment minimizes the number of error sources and simplifies the construction of the device.

A preferred embodiment of the invention comprises calibration of the measuring arrangement. The calibration is performed to ensure the reliability of the measurements. FIG. 6 illustrates the measuring arrangement according to a first preferred embodiment of calibration, and FIG. 7 illustrates the measuring arrangement according to a second preferred embodiment of calibration. The calibration is performed by using a second set PK of reference marks mounted apart from the container, said set comprising at least three reference marks PK1, PK2, PK3 and PK 4 in FIG. 6 or PK11, PK12, PK13 and PK14 in FIG. 7. In the calibration according to FIG. 6, for example, the measuring device 2 is directed in turn to the different reference marks PK1, PK2, PK3, PK4 of the set PK of reference marks; the location of the reference marks PK1, PK2, PK3, PK4 of this second set PK in the coordinate system 10 of the measuring device 2 is determined on the basis of the radiation which is reflected back. The locations of the measuring device 2 and the camera means 1 with respect to each other are calibrated on the basis of the known data on the location of these reference marks PK1, PK2, PK3, PK4 (FIG. 6) or PK11, PK12, PK13, PK14 (FIG. 7) in relation to the camera means 1, or the location data which can be calculated on the basis of the picture information obtained by the camera means 1 (FIG. 7).

According to the preferred embodiment shown in FIG. 6, the set PK of reference marks PK1, PK2, PK3, PK4 used for the calibration is connected to the camera means 1 fixedly in a known manner and directed towards the measuring device 2. The Applicant has found the embodiment of FIG. 6 to be a rapid and reliable method for performing the calibration.

According to the second preferred embodiment of calibration, shown in FIG. 7, the set PK of reference marks PK11, PK12, PK13, PK14 used for the calibration is mounted apart from the camera means 1 and directed to both the measuring device 2 and the camera means 1; the camera means 1 takes a picture of the second set of reference marks PK11, PK12, PK13, PK14, which gives the position of this set PK of calibration reference marks in the coordinate system 11 of the camera means 1. An advantage of this embodiment is that the location of the calibration reference marks with respect to each other does not change. The calibration reference marks PK measured by the measuring device can be the same as the reference marks of which a picture is taken by the camera or they are at least mounted on the same reference mark element.

Generally speaking, the method can also be used for positioning objects other than containers. The object to be measured can thus be other than a container. The method does not have to be applied to measuring wear in a lining or some other coating; it may also be employed for other measurements.

Although the invention has been described above with reference to the examples according to the accompanying drawings, it will be obvious that the invention is not restricted thereto but can be modified in many ways within the scope of the inventive concept disclosed in the appended claims.

I claim:

1. A method for positioning a container for measuring the wear in the container lining, said method comprising: taking a reference picture with a camera means of a set of at least three reference marks mounted on the container, and performing a reference measurement of the container lining with a measuring device emitting and receiving optical radiation, and later in an actual measurement situation, taking a measurement picture of the set of reference marks with the camera means, and performing an actual measurement of the wear in the container lining with the measurement device emitting and receiving optical radiation, and by comparing the measurement picture with the reference picture, calculating correction factors, on the basis of which the actual measurement of the wear in the container lining and the previously made reference measurement of the container lining are combined so as to be represented in the same coordinate system.

2. A method according to claim 1, wherein the relative location and position of the set of reference marks in the coordinate system of the camera means is determined on the basis of the reference picture and the measurement picture by image processing operations, a change in the location and position of the set of reference marks is calculated, and the correction factors are calculated on the basis of said change.

3. A method according to claim 2, wherein, in order to determine the relative location and position of the set of reference marks on the basis of the reference picture and the measurement picture, the location of a reference point, is determined.

4. A method according to claim 2, wherein, in order to determine the change in the location and position of the set of reference marks, the location of individual reference marks is determined on the basis of the reference picture and the measurement picture.

5. A method according to claim 4, wherein, in order to determine the change in the location and position of the set of reference marks, the location of the centres of individual reference marks is determined on the basis of the reference picture and the measurement picture.

6. A method according to claim 1, wherein a reference picture of the set of reference marks is taken and the reference measurement of the lining is made when a container with a new or renewed lining is brought to the measuring site, and a measurement picture of the set of reference marks is taken and the actual measurement of the lining is made when a container with a worn lining is brought to the measuring site.

7. A method according to claim 1, wherein the pictures of the set of reference marks are taken with the camera means in such a way that the image plane of the camera means and the plane formed by the set of reference marks are inclined in relation to each other.

8. A method according to claim 7, wherein the inclination is effected with respect to the three coordinate axes.

9. A method according to claim 7, wherein the inclination between the image plane and the plane formed by the set of reference marks is 20 to 45 degrees.

10. A method according to claim 9, wherein the inclination is about 40 degrees.

11. A method according to claim 1, wherein the picture of the set of reference marks is taken with the camera means from a different direction than the reference measurement of the lining, made with the measuring device.

12. A method according to claim 11, wherein the picture of the set of reference marks is taken with the camera means from the side or from below, and the lining is measured with the measuring device from above.

13. A method according to claim 1, wherein the camera means employed is stationary and has optics with a fixed focal distance.

14. A method according to claim 1, wherein the taking of the reference picture of the set of reference marks and the reference measurement of the lining take place at least approximately simultaneously or successively within a relatively short time.

15. A method according to claim 1, wherein calibration is performed by using a second set of reference marks mounted apart from the container, said set comprising at least three reference marks, and wherein, in the calibration, the measuring device is directed in turn to different ones of the second set of reference marks, and the position of the reference marks of said second set of reference marks in the coordinate system of the measuring device is determined on the basis of the radiation reflected back, and the locations of the measuring device and the camera means with respect to each other are calibrated on the basis of known data on the location of said second set of reference marks in relation to the camera means, or the location data which can be calculated on the basis of picture information obtained by the camera means.

16. A method according to claim 15, wherein the second set of reference marks used for the calibration is connected to the camera means fixedly in a known manner and directed towards the measuring device.

17. A method according to claim 15, wherein the second set of reference marks used for the calibration is mounted apart from the camera means and directed both to the measuring device and to the camera means, and the calibration comprises taking a picture of said second set of reference marks with the camera means for determining the location of the reference marks included in the set of reference marks in the coordinate system of the camera means.

* * * * *